United States Patent
Cherepenin et al.

(10) Patent No.: US 6,236,886 B1
(45) Date of Patent: May 22, 2001

(54) METHOD FOR PRODUCING A TOMOGRAPHIC IMAGE OF THE BODY AND ELECTRIC IMPEDANCE TOMOGRAPH

(75) Inventors: Vladimir Alexeevich Cherepenin; Alexandr Vladimirovich Korjenevsky; Yury Sergeevich Kultiasov, all of Moscow (RU)

(73) Assignee: Technology Commercialization International

( * ) Notice: Subject to any disclaimer, the term of this patent is extended or adjusted under 35 U.S.C. 154(b) by 0 days.

(21) Appl. No.: 09/101,139

(22) PCT Filed: Dec. 5, 1997

(86) PCT No.: PCT/RU97/00398
§ 371 Date: Jan. 14, 1999
§ 102(e) Date: Jan. 14, 1999

(87) PCT Pub. No.: WO98/25519
PCT Pub. Date: Jun. 18, 1998

(30) Foreign Application Priority Data

Dec. 11, 1996 (RU) .................................... 96123647

(51) Int. Cl.[7] ........................................... A61B 5/02
(52) U.S. Cl. ................... 600/547; 128/734; 364/413.13
(58) Field of Search .................................. 600/547, 481, 600/508, 506, 373, 374, 384, 483; 128/734; 364/413.13

(56) References Cited

U.S. PATENT DOCUMENTS

| | | | |
|---|---|---|---|
| 5,184,624 | * 2/1993 | Brown et al. | 128/734 |
| 5,381,333 | * 1/1995 | Isaacson et al. | 364/413.13 |
| 5,544,662 | * 8/1996 | Saulnier et al. | 128/734 |
| 5,626,146 | * 5/1997 | Barber et al. | 128/734 |

FOREIGN PATENT DOCUMENTS

| | | |
|---|---|---|
| 2119520 | 11/1983 | (GB) . |
| 2160323 | 12/1985 | (GB) . |
| 2246634 | 2/1992 | (GB) . |
| 2257530 | 1/1993 | (GB) . |
| 1397024 | 5/1988 | (SU) . |
| 1759402 | 9/1992 | (SU) . |

OTHER PUBLICATIONS

"The Physics of Medical Imaging", Edited by Steve Webb, Adam Hilger, Bristol and Philadelphia, Chapter 8.
V.A. Cherepenin et al, The Electrical Impedance Tomograph: New Capabilities, 1995, p. 430–433.

* cited by examiner

Primary Examiner—Marvin M. Lateef
Assistant Examiner—Jeoyuh Lin
(74) Attorney, Agent, or Firm—Robert W. Becker & Associates

(57) ABSTRACT

The invention is a method of obtaining tomographic images of the human body and the electrical impedance tomograph, in which a source of electric current is used to send electric current at levels undetectable by a human being to pairs of electrodes, between which at least two electrodes are placed. An algorithm of image reconstruction makes it possible to obtain the distribution of absolute conductivity of a body, characterizing the state of soft and bone tissues and blood vessels. The method is fast. It allows one to visualize the changes of conductivity during one cardiocycle and to observe blood filling the heart and vessels. It allows one to obtain time dependence of conductivity of internal areas of the heart, which is an impedance cardiogram, containing additional information about heart function. The use of visualization of conductivity of tissues allows one to observe the processes of internal hemorrhages, to reveal inflammations, to carry out studies of organs of digestion, to observe the state of various tumors, to carry out diagnosis of diseases of the mammary gland, to diagnose various lung diseases. The method allows one to monitor the variation of temperature of internal organs, raising the possibility of diagnosing diseases at early stages. The tomograph is a rather simple, compact device, convenient in operation, safe for a patient and attendants, operating with a standard personal computer. This device can be widely used in medical practice and clinical investigations.

10 Claims, 5 Drawing Sheets

US 6,236,886 B1

METHOD FOR PRODUCING A TOMOGRAPHIC IMAGE OF THE BODY AND ELECTRIC IMPEDANCE TOMOGRAPH

Applicants claim priority based on international application PCT/RU97/00398 filed Dec. 5, 1997 and designating the United States of America.

FIELD OF TECHNOLOGY

This invention provides methods for medical diagnosis using a device to obtain tomographic images of a patient's body.

The device is simple, compact, and convenient to use. It allows tomographic studies to be performed quickly, which is less fatiguing to the patient. The system is safe for the patient and the operator of the device. The images obtained characterize the state of soft and bone tissues and blood vessels. The device allows one to visualize changes in the conductivity of tissues rapidly, for example during one cardiocycle. One can observe blood filling the heart and vessels. The device can determine various characteristics of an organism's state, in particular the time dependence of conductivity of any area of the heart. This is called an impedance cardiogram. The ability to visualize the conductivity of tissues allows one to observe the processes of internal hemorrhages and digestive organs, to study the state of the lungs, to detect various tumors, and to monitor the variation of temperature of internal organs. These capabilities give one the ability to diagnose many diseases at their earliest stages.

BACKGROUND OF THE INVENTION

There are existing methods of obtaining tomographic images of a human body based on the measurement of the spatial distribution of a physical field or radiation that penetrates the object and subsequent reconstruction of the image using the spatial distribution of measured parameters and mathematical methods of convolution and back projection. (The Physics of Medical Imaging. Edited by Steve Webb. Adam Hilger, Bristol and Philadelphia. Chapter 8).

Tomographs, based on the use of x-ray radiation or nuclear magnetic resonance (NMR), are known. (The Physics of Medical Imaging. Edited by Steve Webb. Adam Hilger, Bristol and Philadelphia. Chapter 8).

The known tomographic methods provide high resolution. However, the complicated x-ray or NMR setups used for diagnostics are expensive and difficult in operation, the procedure of inspection is rather long, and the radiation, penetrating a body, is not harmless for patients and operators.

The method of obtaining of a tomographic image of a human body for medical diagnostics, based on the use of electric current, is known as electrical impedance tomography. (Patent of Great Britain 2119520 A, INT CL A61B 5/05, 1983). In the known method a series of contact electrodes is placed on the surface of a patient's body; a source of electric current is connected sequentially to pairs of electrodes; measurements of potential differences (voltages) between pairs of electrodes, arising because of the current flow through the object, are made. Reference values of potential differences are determined based on the assumption of homogeneity of electrical conductivity of the object, or by measuring the same object at different times if the electrical conductivity changes. An image is constructed—from the spatial conductivity distribution of a body or from changes in the conductivity between two measurements—using back projection or the relative differences of measured and reference voltages along equipotential lines of an electric field. It is established that the electrical conductivity of biological tissue depends on its physiological properties. The conductivity distribution of a body can be used to create images of bones, soft tissues and blood vessels.

The electrical impedance tomograph consists of a system of contact electrodes, a unit for electric current excitation, a unit for measurement of potential differences, a microprocessor-based control circuit, a differential amplifier, and analog multiplexers, the inputs of which are connected to contact electrodes and the outputs to the input of the differential amplifier (Patent of Great Britain 2119520 A, INT CL: A61B 5/05, 1983).

However, the use of the method in clinical practice has been hindered until now by the unsolved problem of obtaining absolute or "static" images of satisfactory quality when measurements are carried out on a human body. Existing tomographs allow only dynamic tomograms to be obtained, representing images of conductivity changes between two measurements, which are not informative for medical applications. The inability to visualize static objects is due to the inability to completely solve the inverse problem of the conductivity reconstruction due to the difficulty of obtaining reference values of potential differences when neither the geometry of the boundary surface of the object studied nor the location of measuring electrodes on this surface are known exactly.

Visualization of the absolute conductivity distribution in the cross-section of a human body with a high rate of data acquisition became possible by using a compact tomograph with control of all of its measuring functions by personal computer. The computer carries out processing, visualization and storage of data. (V. A. Cherepenin, A. V. Korjenevsky et al. The Electrical Impedance Tomograph: New Capabilities.//IX International Conference on Electrical Bio-Impedance, Proceedings.—Heidelberg, 1995, p. 430–433). The method of obtaining a tomographic image of a body described in this reference involves: the placing of a series of contact electrodes on the surface of a body; the sequential dipole connection of an electric current source to pairs of adjacent electrodes; the measuring of potential differences between each pair of the rest of the electrodes; the determination of reference values of potential differences; and the reconstruction of the image of spatial distribution of conductivity of a body by back projection of weighted relative differences of the reference and measured voltages along equipotential lines. Reference values of potential differences $$u_r^i(j)$$

are determined by approximation of the measured distribution of potential differences $$u_m^i(j)$$

according to the expression:

$$u_r^i(j) = c_1^i f_1^i(j) + c_2^i f_2^i(j) + c_3^i, \quad (1)$$

Where:

i—the number of exciting pairs of electrodes;

j—the number of measuring pairs of electrodes;

$$f_1^i(j) -$$

given distribution of voltage between the adjacent electrodes along the boundary of the reference object;

$$f_2^i(j) -$$

signals caused by spurious couplings; and $$c_\alpha^i (\alpha = 1, 2, 3) -$$

approximation coefficients of the measured distribution of potential differences $$u_m^i(j).$$

In the described solution it is possible to construct a reference data set which does not contain information about the interior structure of the object by using an approximation of the measured data $$u_m^i(j)$$

by smooth dependencies from a set of simple linearly independent functions. This set, together with an initial set including variations that characterize the interior structure of the object, is used for reconstruction of the absolute conductivity of the object. The measured potential differences can contain considerable systematic errors caused primarily by spurious penetration of signals from channel to channel in the integral multiplexers and input circuits of the tomograph. During the reconstruction of the distribution of spatial conductivity, these noises cause the appearance of artifacts and significantly reduce the quality of the image. To eliminate their influence, a set of spurious signals can be included in the set of base functions used for approximation of the input data. Best results are obtained by using a combination of three functions mentioned in equation (1). The distribution $$f_1^i(j)$$

is the distribution of voltage between the adjacent electrodes along the boundary of a cylindrical object with homogeneous conductivity when an electric current source is connected to the pair of adjacent electrodes.

The developed algorithm for the reconstruction of the conductivity distribution allows one to obtain medically useful and informative "static" images characterizing the physiological state of organs and tissues. However, the low sensitivity and rather low resolution of this method limits the range of its application.

SUMMARY OF THE INVENTION

In the present invention the method of obtaining a tomographic image of a human body is presented. It allows one to obtain qualitative visualization of conductivity inside a body with high sensitivity and satisfactory resolution, dynamically characterizing the state of internal organs and tissues with high reliability. The method can increase the signal-to-noise ratio more than one order of magnitude and thus increase the sensitivity and resolution of the tomographic device. The device is suitable for wide spread use in medical practice and clinical investigations. The method presented here reveals and measures structures and processes, determination of which is difficult or impossible by use of x-rays or nuclear magnetic resonance. The method allows easy and safe diagnosis of a patient not only in clinical environments but also in physicians' offices and in laboratories.

The problem of increasing the quality of tomographic images is solved by the development of a new effective method for measuring the potential differences and for reconstructing the image of the spatial distribution of conductivity found inside a body.

The invention is the method of obtaining a tomographic image of a body, including the placing of a series of contact electrodes on the surface of a human body, connecting the electric current source to pairs of electrodes sequentially, measuring the potential difference between each pair of electrodes, determining the reference values of the potential differences $$u_r^i(j)$$

by the approximation of measured distribution of the potential differences $$u_m^i(j)$$

in accordance with the expression $$u_r^i(j) = c_1^i f_1^i(j) + c_2^i f_2^i(j) + c_3^i$$

while the electric current source is connected to those pairs of electrodes, between which at least two electrodes are placed, and the reconstruction of the image of spatial distribution of the conductivity of a body by back projection along equipotential lines, made according to the following expressions:

$$S = \sum \frac{W^{lt} W^{rt}}{W^{lt} + W^{rt}} (\lambda^{lt} + \lambda^{rt}),$$

$$\lambda^{lt,rt} = u_r^{lt,rt} / u_m^{lt,rt} - 1, \text{ where:}$$

$W^{lt}$, $W^{rt}$—weight factors determined according to the procedure of back projection in the direction from the "left" and from the "right" intersection of equipotential lines with the surface of a body, correspondingly, $\Sigma$—a summation over all positions of the injecting electrodes, $$u_m^{lt,rt}, -$$

voltages, measured on the left and on the and right "ends" of equipotential lines, which pass through the given point of a reconstructed cross section, $u_r^{lt,rt}$, — reference potential differences corresponding to a body with homogeneous conductivity,
- i—the number of exciting pairs of electrodes,
- j—the number of measuring pairs of electrodes,
- $f_1(j)$—given distribution of voltage between adjacent electrodes along the boundary of a reference object, $f_2^i(j)$ — signals caused by spurious couplings, and $c_\alpha^i (\alpha = 1, 2, 3)$ — approximating coefficients of the measured distribution of the potential differences $u_m^i(j)$.

The best result for increasing the sensitivity of the devices is obtained when the polar injection of electric current by a pair of diametrically opposite electrodes is used.

The accuracy of measurements is also increased by carrying out measurements on a certain pairs of electrodes while the electric current source is connected sequentially to each pair of other electrodes. The procedure of connection is then repeated sequentially by making measurements on the next pair of electrodes.

It is efficient to determine the signals $f_2^i(j)$, caused by spurious couplings, by measurement.

For the diagnosis of organ functions when the conductivity varies in time, a series of measurements of the potential differences is automatically made sequentially in time, a spectral Fourier transformation of time dependencies of the measured results is carried out, and the reconstruction of the images of the spatial distribution of conductivity of the organs for each frequency component is made.

To obtain an electrical impedance cardiogram, a series of measurements of conductivity of various areas of a heart is made, and the time dependence of this conductivity is determined.

The reconstruction of the image of spatial distribution of absolute conductivity of a body is carried out by normalizing the measured conductivity values on the assumption that the least value of conductivity corresponds to the conductivity of bone tissues and the greatest value of conductivity corresponds to the conductivity of blood.

The invention can be used to diagnose cardio-vascular disease, to identify internal hemorrhages and tissue inflammation, to detect tumor formation in its early stages, and to determine the temperature of internal organs. It can be used to diagnose diseases of bone tissues. It can safely and simply diagnose diseases of the mammary gland.

According to the invention, the electrical impedance tomograph consists of: a system of contact electrodes; a unit for the excitation of electric current; a source of constant voltage; a unit for measuring potential differences; a microprocessor-based control circuit; a differential amplifier; analog multiplexers; a circuit for the compensation of the common-mode component of voltages on each pair of electrodes; a circuit for compensation of contact potential differences on each electrode; and a circuit for control of the quality of contacts where the inputs of the analog multiplexers are connected to contact electrodes, the outputs to the input of the differential amplifier. A circuit for the compensation of the common-mode component of voltages can be composed of a feedback circuit containing the operational amplifier. The output of the common-mode signal of the differential amplifier is connected to the inverting input of the operational amplifier, the output of which is connected to the unit for excitation of electric current. The circuit for control of contact quality is composed as two comparators, the first inputs of which are connected to the output of the unit for excitation of current. The second input of one comparator is connected to the positive output of the constant voltage source. The second input of another comparator is connected to the negative output of the constant voltage source. The outputs of the comparators are connected to the microprocessor based control circuit.

It is expedient to compose the compensation circuit for the contact potential differences as a feedback circuit, that includes an analog switch and an integrator connected in series. The analog switch input is connected to the measuring unit, and the output of the integrator is connected to the zero correction input of the differential amplifier.

The present invention improves on previous solutions in that an optimal method of measurement and a new algorithm of reconstruction of conductivity distribution have been found, providing a quality image with high resolution.

During measurements of a human body the value of injected current is limited to safe levels. Therefore, the value of the measured signals is found to be rather small. The quality of reconstructed images is seriously influenced by the ratio of the amplitude of the measured signals to the value of noises of the device and external electrical noises on the frequency of the measurements. In the present invention the signal-to-noise ratio is increased by more than an order of magnitude by the injection of the electric current through pairs of electrodes separated by at least two electrodes. This allows increased sensitivity and, in many cases, increased resolution.

For this more general case, compared with dipole injection, it is necessary to correct the method of reconstruction of the image of the spatial distribution of conductivity. Initial data consist of the potential differences between adjacent electrodes when the current source is connected to some pair of electrodes which are fixed on the patient's skin along a closed contour, wrapping around the body. Using N electrodes, we have N profiles corresponding to a particular variant of the connection to the current source, each containing (N-4) values of the potential differences between free pairs of electrodes.

The back projection procedure for the arbitrary method of injection of current is described in the following way:

$$S = \sum \frac{W^{lt} W^{rt}}{W^{lt} + W^{rt}} (\lambda^{lt} + \lambda^{rt}),$$

$$\lambda^{lt,rt} = u_r^{lt,rt} / u_m^{lt,rt} - 1,$$

where:
- $W^{lt,rt}$—weight factors, calculated according to the usual procedure of back projection in the direction from the "left" and from the "right" intersections of the equipotential lines with the body's boundary correspondingly, Σ—the sum over all positions of the injecting electrodes, $$u_m^{lt,rt} -$$

voltages, measured on the left and on the right "endpoints" of equipotential lines, passing through the given point of a reconstructed cross-section, $$u_r^{lt,rt} -$$

reference potential differences corresponding to a body with homogeneous conductivity.

In the present invention, accuracy of measurements and reconstructed image quality are improved by the correct choice of the sequence of contact switching, within the same strategy of the injection of current, through the reduction of the influence of transitory processes that arise in the input circuits of the receiver from one pair of electrodes to another, without decreasing the fast operation of the device. During measurements, the receiver is switched only after measurements with all possible pairs of injecting electrodes are completed. Unlike known systems, where for fixed positions of the injecting electrodes, sequential switching of the measuring electrodes is made, in the present invention the receiver is connected to the same pair of electrodes for a long time, while frequent switches are made on the injecting pair. The transient processes are completed early in the series of measurements, and their influence is reduced significantly, while the same total time is required for a complete set of measurements. For a system with 16 electrodes, the influence of these transients by the time measurements on a given pair of electrodes is completed is $e^{12} \approx 10^5$ times smaller than in all the known solutions to the problem. Moreover, measurement errors are further decreased by the use of a circuit to control the quality of contacts.

BRIEF DESCRIPTION OF THE DRAWINGS

The invention is illustrated in the following drawings.

Figure 1:
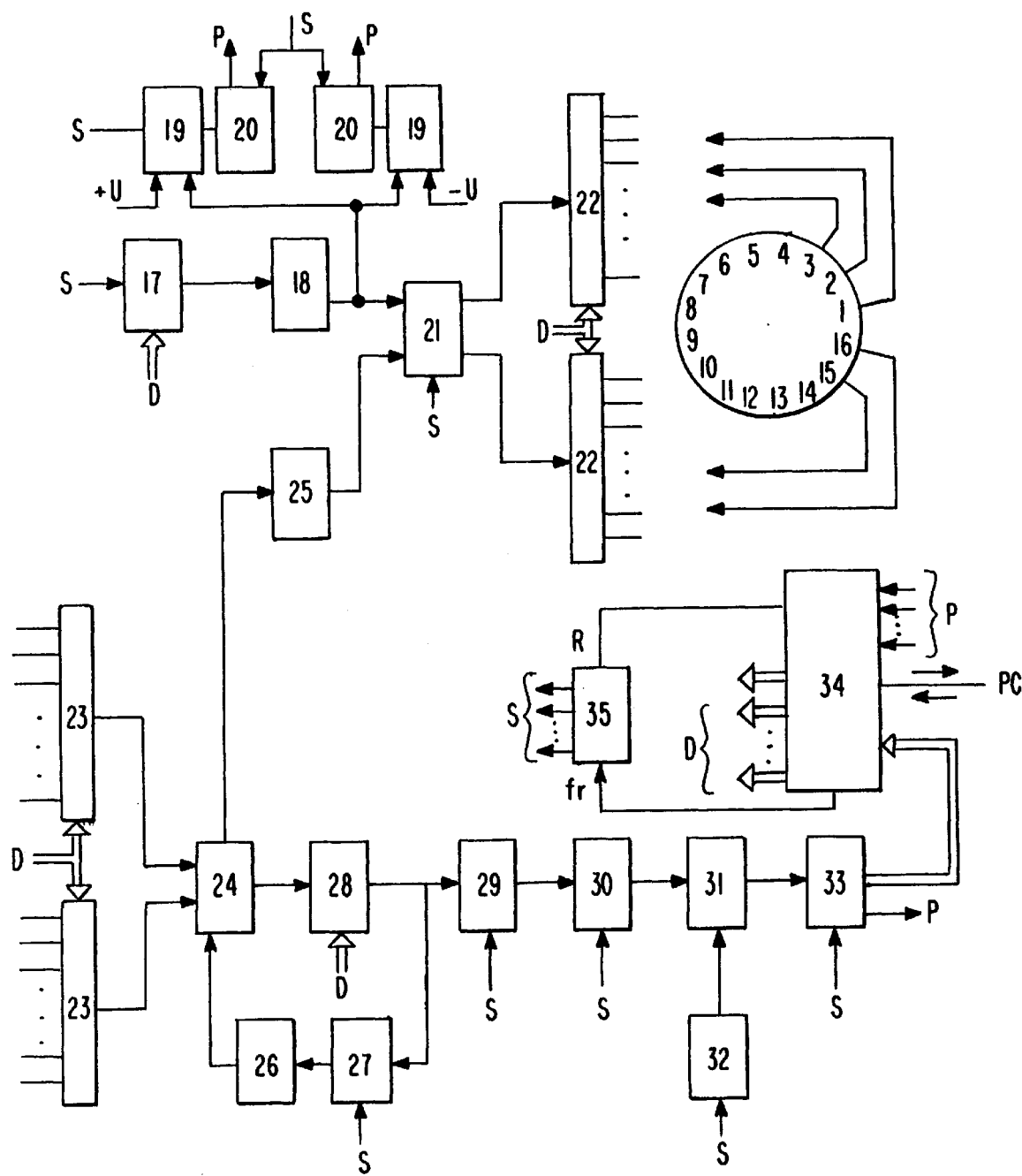
FIG. 1 is a block-diagram of the tomograph's measuring system.

The block-diagram of tomograph (FIG. 1) is coded as follows: contact electrodes 1–16, generator of pulsing voltage 17, voltage-to-current converter 18, comparators 19, triggers 20, pulse phase modulator 21, analog multiplexers 22 and analog multiplexers 23 with leads for connections to electrodes, differential amplifier 24, common mode feedback amplifier 25, integrator 26, analog switch 27, amplifier stage 28, lock-in detector 29, switch 30, integrator 31, switch 32, analog-to-digital converter (ADC) 33, microprocessor 34, control signal generator 35.

The operation of the system of data acquisition of the impedance tomograph measures the potentials on the surface of a human body with the aid of contact electrodes 1–16 upon the injection of a weak electric current. The exciting pair of electrodes is connected to a current source; other pairs are used for the measurements of voltages caused by the flow of the current in the exciting electrodes. This variant of the impedance tomograph is constructed under a single-channel scheme and is designed for operation with 16 electrodes. The duration of each measurement is 350 µS, and the frequency of fulfifllment of complete cycles of measurements is 11 frames per second. Measurements are carried out upon the occurrence of a pulsing signal of a special form having an average frequency of 8 kHz. The use of this signal simplifies the equipment and permits higher accuracy and faster operation compared to previously existing systems that use sinusoidal excitation.

The excitation circuit contains a high-precision generator of pulsed voltage 17, a voltage-to-current converter 18 and a pulse phase modulator 21. The generator 17 produces pulsed voltage in the form of two periods of meander, shifted on 180°, with controlled amplitude which is established by an 8-bit code from the microprocessor unit 34. The use of this pulsed current in the tomograph eliminates the need for a high-precision sinusoidal signal generator. The voltage-to-current converter 18 is based on two operational amplifiers. It has a stable gain coefficient, high output resistance, and it provides output current values that are independent of the resistance of the circuit of exciting electrodes. During measurements, the quality of the electrical contact between the electrodes and skin can become poor. This leads to errors in the measurements arising from disturbance in operation of the current source, when the maximum permissible output voltage is reached, as well as from increasing noise and errors in the input circuits of the receiver. Therefore, it is important to be able to control the quality of contacts between electrodes and skin during measurements and to determnine which contact shows increased electrical resistance and, therefore, requires intervention. To achieve this, two comparators 19 are introduced in the circuit of the device, which compare the output voltage of the voltageto-current converter with given constant positive +U and negative −U voltages, which are equal to the maximum allowable positive and negative output voltage of the current source. The output signal of comparators 19 corresponding to voltages falling outside of the allowable limits is transmitted to the microprocessor block 34 for further processing. The output signal from comparators 19, corresponding to the deviation of the voltage from allowable limits, is received by the mnicroprocessor and, together with the current addresses of the active contacts, is transmitted to the personal computer. This results in a message to the user displayed on the computer screen giving the location of the electrodes that are showing poor contact and require attention In order to maintain a short signal about poor contact on the output of the circuit after the current pulse and to evaluate it by the microprocessor, the triggers 20 are connected to the outputs of the comparators. These triggers are set when the comparators come into action and are reset by the microprocessor before the next pair of electrodes are engaged and processed. As the triggers 20 made with CMOS technology have a stable level of coming into action at about half of the supply voltage, they also can work as comparators. For the negative half-period overrun of the signal to register, it must be applied to one of the triggers through an inverter.

The pulse phase modulator 21 is based on analog switches and provides a 180° alteration of phase of the output signal of the excitation circuit once during the period of measurements. Selected pairs of electrodes are connected to the excitation circuit by two analog multiplexers 22 with a common control address bus. The system of contact electrodes 1–16 is connected to multiplexers 22 in such a way that a pair of active electrodes are always diametrically opposite electrodes (polar excitation mode). Voltage from the receiving pairs of electrodes 1–16 of the contact systems is transmitted to the amplifier block of the tomograph via analog multiplexers 23.

The useful information is contained in the differential component of the voltage measured between a pair of receiving electrodes. Differential amplifier 24 must suppress the common-mode component of these voltages. Because it is impossible to achieve complete suppression of the common-mode component, we introduced a negative feedback loop with respect to the common-mode component, based on an operational amplifier 25. On the inverting input of this amplifier the common-mode component from the pair of measured voltages is transmitted, and its output is connected to the exciting pair via the modulator 21. The measured differential signal is superimposed by the contact potential difference, which amounts to ±300 mV for the stainless steel electrodes used in our experiments. Because this value may significantly exceed the dynamic range of the amplifier (the useful signal amplitude amounts to tens or hundreds microvolts), the contact potential difference must be compensated. The function of measurement and storage of the values of the contact potential difference is performed by integrator 26 in combination with analog switch 27. The output voltage of integrator 26 enters the zero correction input of the differential amplifier 24. Because the range of measured voltages is sufficiently large, we introduced circuit 28 with controlled gain in order to initially reduce the dynamic range of the signal. Using this circuit, the total gain can be controlled within three orders of magnitude by a code transmitted from the microprocessor 34 via a control bus.

The amplified voltage passes via a lock-in detector 29 and switch 30 to the integrator 31. When the measuring cycle is completed, the voltage, accumulated at the output of integrator 31, allow us, taking into account the gain of circuit 28, to determine the signal on the receiving pairs of electrodes. The signal from the integrator 31 enters an analog-to-digital converter (ADC) 33, the output 12-bit binary data from the ADC are transmitted to the microprocessor 34. During the time of ADC operation, integrator 31 is switched by switch 30 into the storage regime, and the initial state is set prior to the next measurement cycle by switch 32. This mode of connection of the lock-in detector and integrator made the results of measurements less affected by low-frequency or high-frequency noise components presented in the spectrum of the measured signal.

Operation of the analog circuit is controlled by logical signals of the S group supplied from the generator 35, and by the command groups D produced by the microprocessor unit 34. Generator 35 contains a counter of the clock pulses $f_T$, and a read-only-memory (ROM) unit, and it is set into its cyclic operation regime by a logical level of signal R supplied from the microprocessor 34.

The microprocessor system controls a considerable number of operations of the analog circuitry of the tomograph, provides a link between the tomograph and the personal computer (PC), and allows the user to modify the tomograph's configuration.

For demonstration and analysis of reconstructed images, data are stored in archive. Images can be viewed one frame at a time or with successive frames displayed continuously ("movie mode"). Individual frames can be increased in size on the screen. Up to eight frames can be displayed on the screen at once. Reconstructed frames can be spectrally analyzed when a series of measurements is obtained in automatic mode. In this case one can see the spatial distribution of amplitude of definite frequency harmonics in the static, one frame regime and the evolution of the image at the same frequency, taking into consideration the phase of oscillations in each mode, in the "movie mode".

Measurements were performed on various locations of a human chest and extremities. The working electrodes were 30-mm diameter stainless steel disks coated with the gel for electrocardiography. The electrodes were fixed with the help of an elastic belt. Some measurements were performed using one-shot (expendable) electrodes of the Blue Sensor M-00-A type (Medicotest, Denmark). These electrodes provide lower contact resistance and contact potential difference, but the data acquisition system of the tomograph and the reconstruction algorithm employed made the results of visualization sufficiently independent of the quality of contacts.

The advantages of the method presented here over previous inventions can be shown quantitatively. If the value of noises is considered constant for a concrete measuring device, the amplitude of signals and, therefore, signal-to-noise ratio depends strongly upon the techniques used to acquire measurements. To illustrate, one can compare the ratio of minimum amplitudes of signals, measured on a pair of adjacent electrodes, in the case of dipole current injection (for example, for a system with sixteen electrodes, through electrodes 1 and 2—see FIG. 1), polar injection (for example, through electrodes 1 and 9) and injection through two electrodes, between which two other electrodes are placed (for example, through electrodes 1 and 4) for a cylindrical object with homogeneous conductivity distribution. In all cases, the injecting current has the same value. In the case of dipole injection and injection through separated electrodes, the minimum signal is measured on pairs of electrodes which are diametrically opposite to the active pair (electrodes 9–10 and 10–11, correspondingly). In the case of polar injection, the minimum signal is measured on four pairs of electrodes placed symmetrically between two injecting (active) electrodes—electrodes 4–5, 5–6, 12–13 and 13–14. Assuming that the than the diameter of the studied object, and using elementary geometrical relations, we obtain an estimation of the ratio of minimum amplitudes of measured signals for polar $_p$ and dipole $_d$ injection: $_p/V_d \approx 2\sqrt{2}D/d$, where D—diameter of object (a circle on which electrodes are placed), and d—distance between adjacent electrodes.

For the system with 16 electrodes, this ratio is 14.4. More precise calculations give the coefficient 15.2 (a close ratio between the amplitudes of the measured signals is also obtained experimentally by measurements on a human thorax). When injection occurs through two electrodes, between which two other electrodes are placed, the minimum signal is measured on the pair of electrodes most distant from the injecting pair (electrodes 10–11). Calculations in this case show an increase of 3.2 times the minimum amplitude of the signal, compared with dipole injection. Increasing of number of electrodes further increases the ratio of amplitudes of measured signals for non-dipole and dipole injection. Therefore, the use of polar injection in the system with 16 electrodes produces an increased signal-to-noise ratio of more than an order of magnitude, thus increasing the sensitivity and, in many cases, the resolution of the device.

Figure 2:
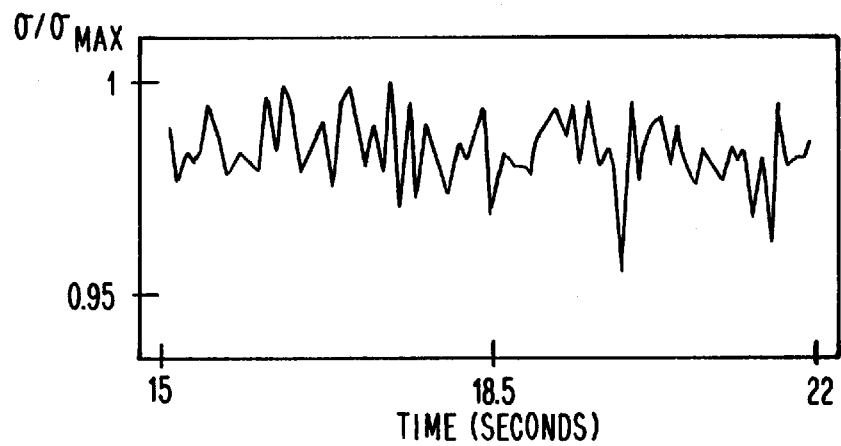
FIG. 2 shows the time dependence of the conductivity of the interior of a heart, which is obtained by measurement with dipole injection, as in previously invented solutions.
Figure 3:
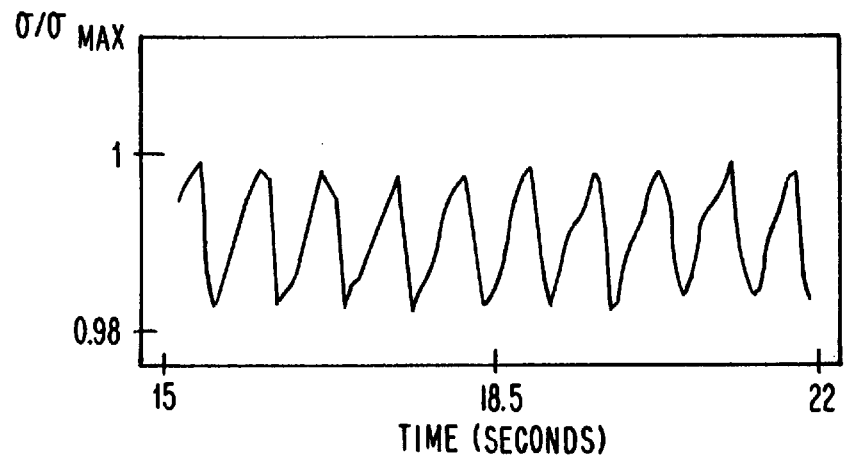
FIG. 3 shows the same dependence as FIG. 2 using the polar injection method described in this patent application.

To illustrate improvements in the polar injection tomography over dipole tomography, we present time dependencies of heart conductivity obtained by using dipole injection (FIG. 2) and polar injection (FIG. 3). Polar injection reliably shows changes of conductivity, caused by changes in the blood filling the heart. This allows the researcher to determine the frequency of heart's rhythm and to estimate the volume of blood ejected by heart. Inages produced using dipole injection of current are considerably noisier. This makes determination of the frequency of heart's contractions and the volume of blood more difficult. The resulting measurements are not suitable for diagnostics.

Let's estimate quantitatively the accuracy of measurements and the quality of reconstructed images using the present invention, produced using the correct choice of contact switching sequences, when the mode of current injection doesn't change. After switching the receiver from one pair of contacts to another, a transient process occurs in the input circuits due to different values of galvanic potential differences on the contacts. This transient process may not be completed by the time measurements of potential difference on electrodes have begun. This will cause errors due to the presence of a component on the operation frequency of a tomograph in the spectrum of this process. The influence of this process on the results of measurements is large, because galvanic voltage steps, occurring when electrodes are switched, amount to hundreds of millivolts, and they significantly exceed the minimum amplitude of measured signals by tens or hundreds microvolts. The influence of transient processes can be decreased by increasing the time delay between the moment of switching of a measuring pair of electrodes and the beginning of measurements. However, this will slow the operation of the system.

It is possible to reduce the influence of transients without reducing the speed of device operation if during measurements the receiver is switched from one pair of contacts to the other only after completion of measurements with all possible pairs of injecting electrodes. The transient process is completed at the very beginning of the series of measurements, and its influence is reduced significantly with the same total time required for completion of a full set of measurements. For the system with 16 electrodes and polar injection of current, the total duration of measurements without switching measuring pairs of electrodes increases 12 times using this mode of operation. The influence of the transient process up to the moment of completion of measurements on a given pair of electrodes is $e^{12} \approx 10^5$ times smaller.

BEST EMBODIMENT OF THE INVENTION

Figure 5:
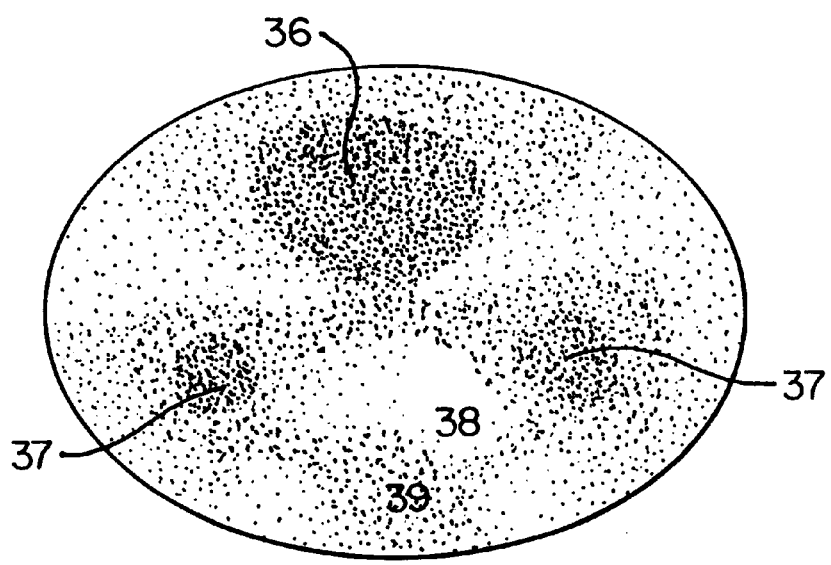
FIG. 5 shows the impedance tomogram of the thorax of patient Y.

Example 1. FIG. 5 shows the reconstructed distribution of conductivity in a cross-section of the thorax of patient Y. Measurements were carried out using polar injection of current. The spinal column 36, lungs 37, heart 38, and breastbone 39 are clearly visible. Large blood vessels can be identified. The use of the adaptive algorithm of reference data synthesis for image reconstruction makes it impossible to obtain quantitative information about conductivity directly from the results of reconstruction. We normalized images, using the known values of the conductivity of bone tissues and blood (or close values of the conductivity of muscle along the fibers). During the normalization, a point with minimum conductivity is determined on the image and ascribed bone tissue with a conductivity of 0.01 S/m. The point with maximum conductivity is ascribed a blood conductivity (0.5 S/m). The other values range between the two limits. The conductivity of lungs, obtained upon this image calibration, agrees quite well with the results of direct measurements.

Figure 6:
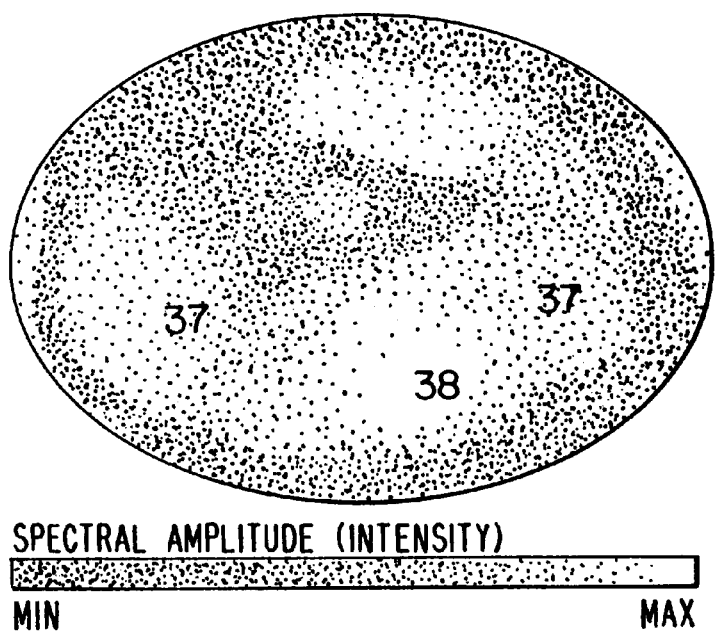
FIG. 6 shows the spatial distribution of the spectral amplitude of conductivity in the cross-section of the thorax at the frequency corresponding to the frequency of heart contractions of patient Y.

When a series of measurements is performed using the automated regime (with equal time intervals between measurements), obtained temporal variations can be studied by use of Fourier analysis. FIG. 6 shows a spatial distribution of the amplitude of a spectral component of conductivity with a frequency corresponding to the frequency of heart contractions, calculated for the same series of measurements from which a static frame is obtained. Spectral data processing has increased the contrast of the regions of the heart, blood vessels and a portion of the lungs, where pulsations of conductivity are the most intense due to circulation of blood.

Figure 4:
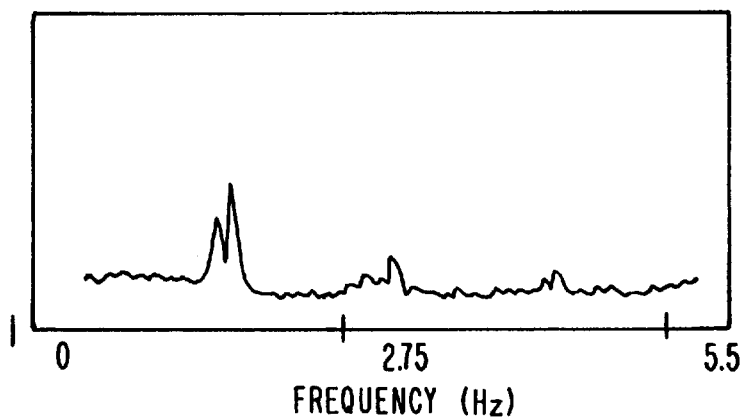
FIG. 4 shows the spectrum of this dependence.

FIG. 3 presents the time variation of conductivity for the point of the image inside the heart (corresponding to heart's interior). This is an impedance cardiogram, which provides additional information about heart function. FIG. 4 shows a spectrum of this dependence. The first maximum corresponds to the frequency of heart contractions; two other peaks correspond to its harmonics. These characteristics open new possibilities in cardiology because they contain parameters that directly characterize the function of heart. They allow the researcher to estimate the volume of blood ejection by the heart, to determine the frequency of the heart's rhythm, and to define more exactly blood filling in various parts of heart.

Figure 7:
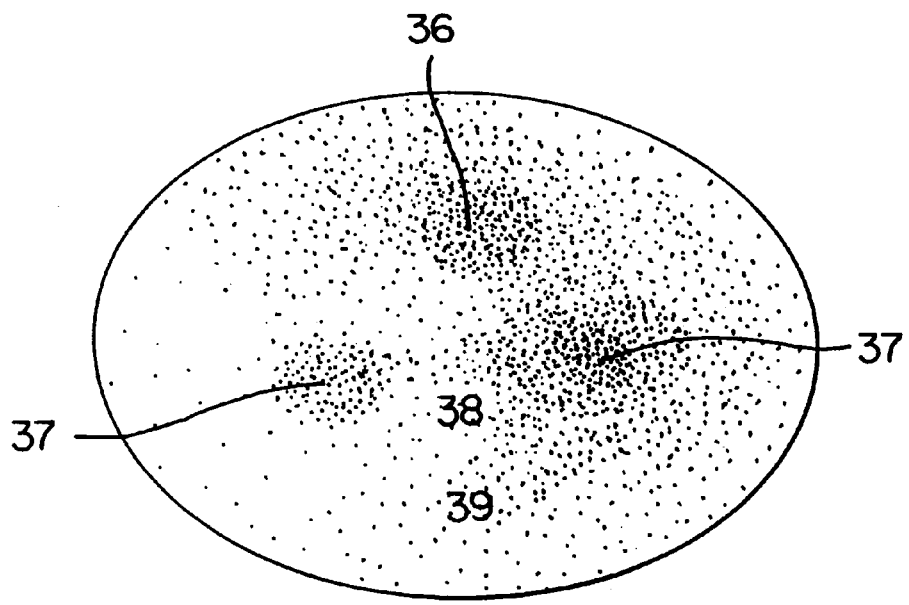
FIG. 7 shows the impedance tomogram of the thorax of patient X.
Figure 8:
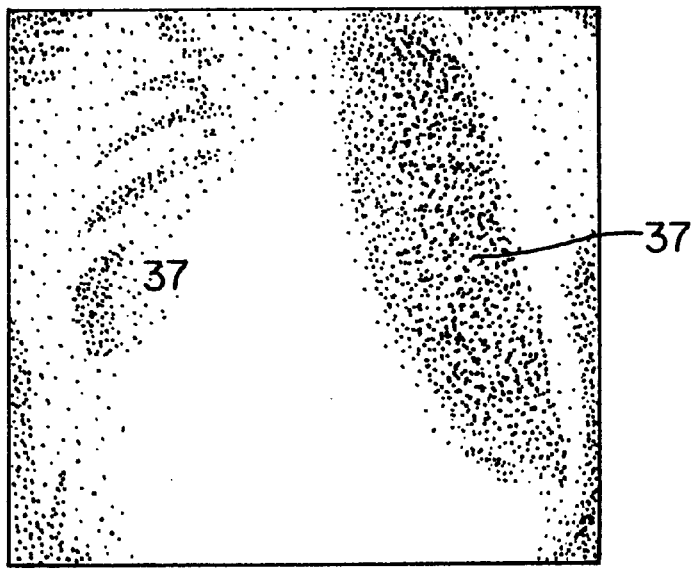
FIG. 8 presents a summarized roentgenogram (X-ray photograph) of the thorax of patient X.

Example 2. Patient X has a diagnosis of central cancer of the right lung, chronic sclerotic bronchitis. Roentgenography (FIG. 8) showed a decrease in area of the right lung, transparency of the upper part of right lung is reduced, and the left lung is transparent. On the electrical impedance tomogram (FIG. 7) one can distinctly see the change of conductivity of the right lung—a virtual absence of air filling in the measured cross-section. Light areas of the image in the area of the right lung indicate that conductivity of these areas is high because of replacement of low-conductivity lung tissue by dense tissue formations (primary tumor, metastasis and increased lymphatic nodes), and because of the presence of liquid (hydrothorax). The increase in the area and the density of the image of the left lung points to an increase in air filling the area to compensate for breathing inefficiency caused by the disease. The results of electrical impedance tomography have good correlation with Roentgenography data (FIG. 8) and reveal changes in the lungs more clearly.

Use of tomography for the diagnosis of various tumors offers the potential for improved treatment of oncologic diseases and for the diagnosis of diseases of the mammary gland.

Figure 9:
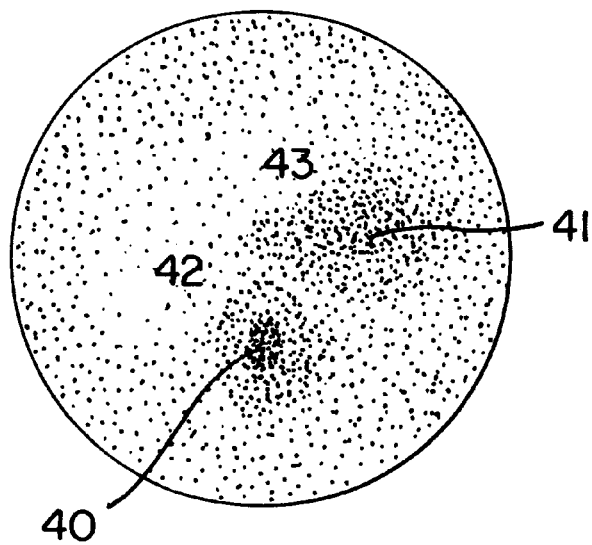
FIG. 9 shows the impedance tomogram of the lower part of the left leg of patient Z.
Figure 10:
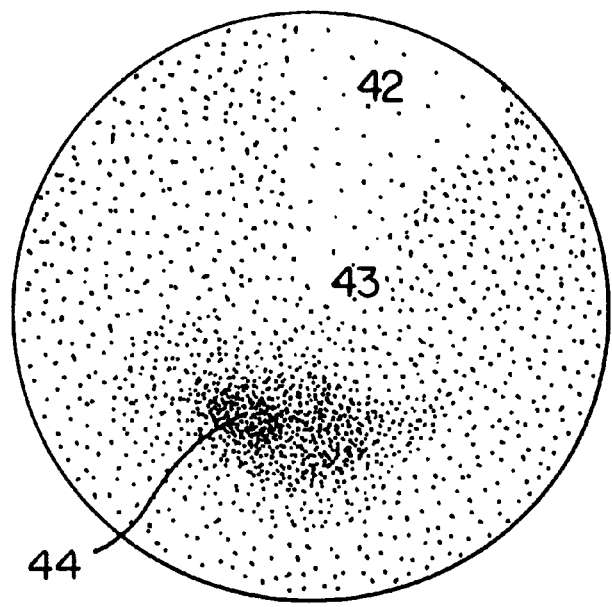
FIG. 10 shows the impedance tomogram of the upper part of the left leg of patient Z.

Example 3. FIGS. 9, 10 show the impedance tomogram of the lower and upper parts of the left leg of patient Z, where tibia 40, fibula 41, muscles 42, blood vessels 43 and femur 44 are clearly visible. Investigations revealed that it is possible to determine the changes of conductivity of vessels due to varicose or thrombosis. This example demonstrates the potential to diagnose cardiovascular diseases and diseases of bone tissuesoke-arthrosis, fractures and others. Changes in physical loading leads to significant changes of muscle conductivity due to changes of temperature and blood flow.

This invention can determine changes in the temperature of internal organs, because Temperature changes are accompanied by change in conductivity of tissues. This could allow rapid identification of inflammations due to infections and other conditions.

PRACTICAL APPLICATIONS

A rather simple, relatively inexpensive device, linked with a standard personal computer, to create tomographic images based on the electrical impedance of an object can be made. Measurements are safe for patient and attendants. The conductivity distribution reconstruction algorithm allows one to visualize high quality, informative images with the help of a tomograph familiar in look and presentation in the field of medicine. Results obtained by reconstruction of absolute conductivity in vivo show that electrical impedance tomography can be widely used in medical practice and clinical investigations.

The method presented here can also be used to reveal and measure structures and processes. Visualization of the conductivity of tissues makes it possible to observe the processes of internal hemorrhages and inflammatory processes. The distinctions in conductivity of fat tissues and muscles will allow the researcher to define the distribution of muscle tissues. The specific conductivity of lungs at inhalation and exhalation differs three times because of changes of air filling the lungs; thus emphysema diagnosis is possible. Appreciable changes in tissue conductivity occur as a result of necrosis and changes in the density of tissues, improving the study of the behavior of tumors during treatment of cancer patients.

In comparison with x-ray or NMR tomography electrical impedance tomography is more rapid, it allows the researcher to visualize the changes of conductivity during one cardiocycle and to observe blood filling the heart and vessels. Inflammations and some other pathological processes are accompanied by an increase in the temperature of tissues. The tomograph allows one to determine the temperature of interior organs and to diagnose many diseases at an earlier stage.

The high sensitivity of the method to variations of physiological condition of tissues and organs, good contrast in the obtained images, high rate of measurements, safety for attendants and patient, low cost of the device and simplicity of operation indicate the invention could have wide application in medical practice.

We claim:

1. A method for the construction of images of a body using electrical impedance tomography, comprising:
    a) placing a series of contact electrodes at spaced intervals on the surface of a body;
    b) selecting a pair of electrodes for a set of potential difference measurements, each measurement made by connecting an electric current source to pairs of non-selected electrodes sequentially, said pairs of electrically connected electrodes being separated by at least two other electrodes;
    c) selecting different pairs of measurement electrodes and repeating step b) for each pair until all pairs of measurement electrodes had been selected;
    d) determining the reference values of the potential differences $$u_r^i(j)$$

by the approximation of the measured distribution of the potential differences $$u_m^i(j)$$

in accordance with the expression $$u_r^i(j) = c_1^i f_1^i(j) + c_2^i f_2^i(j) + c_3^i$$

while the electric current source is connected to the $i^{th}$ pair of electrodes, and where i is the number of the exciting pair of electrodes, j is the number of the measuring pair of electrodes, $$f_1^i(j)$$

is the given distribution of voltage between adjacent electrodes along the boundary of the reference object, $$f_2^i(j)$$

are signals caused by spurious couplings, and $$c_\alpha^i (\alpha = 1, 2, 3)$$

are the approximating coefficients of the measured distribution of the potential differences; and
    e) reconstructing the image of the spatial distribution of conductivity of said body by back projection along equipotential lines according to the expressions:

$$S = \sum \frac{W^{lt} W^{rt}}{W^{lt} + W^{rt}} (\lambda^{lt} + \lambda^{rt})$$

$$\lambda^{lt,rt} = u_r^{lt,rt} / u_m^{lt,rt} - 1$$

where $W^{lt}$, $W^{rt}$ are weighting factors determined according to the procedure of back projection in the direction from the left and from the right intersection of the equipotential line with the surface of said body, S is summed over all positions of the injecting electrodes, $$u_m^{lt,rt}$$

are voltages measured on the left and on the right ends of the equipotential line that passes through the given point of the reconstructed cross section, and $$u_r^{lt,rt}$$

are the reference potential differences corresponding to a body with homogeneous conductivity or determined according to claim 1d.

2. The method of claim 1, wherein said electric current source is connected to a pair of diametrically opposite electrodes.

3. The method of claim 1, wherein said electric current source is produced by a pulsed voltage in the form of two periods of meander, shifted by 180 degrees in phase with a controlled amplitude that is established by an 8-bit code.

4. The method of claim 1, wherein the signals caused by spurious couplings are determined by measurement.

5. The method of claim 1, wherein a series of electrical impedance tomographs are produced sequentially in time of a body in which the conductivity varies in time and a spectral Fourier transformation of the time dependencies is obtained, thereby permitting the reconstruction of the images of spatial distribution of conductivity of the body for each frequency component.

6. The method of claim 1, wherein the reconstruction of the image of the spatial distribution of absolute conductivity of a body is carried out by normalizing the obtained conductivity values on the basis that the least value of conductivity corresponds to the conductivity of bone tissues and the greatest value of conductivity corresponds to the conductivity of blood.

7. An electrical impedance tomograph device, comprising:
   a. a plurality of contact electrodes positioned adjacent to the surface of a body at spaced intervals;
   b. current source means to inject current into a pair of excited electrodes separated by at least two other electrodes;
   c. means to measure potential differences in other electrodes pairs induced by said pair of excited electrodes such that measurements can be made on a given pair of electrodes while said current source is connected sequentially to each pair of the remaining electrodes and this measurement procedure is repeated on each of the remaining electrode pairs;
   d. circuit means to compensate for the contact potential differences on each electrode;
   e. computer means to determine the reference values of the potential differences $$u_r^i(j)$$

by the approximation of the measured distribution of the potential differences $$u_m^i(j)$$

in accordance with the expression $$u_r^i(j) = c_1^i f_1^i(j) + c_2^i f_2^i(j) + c_3^i$$

while the electric current source is connected to the $i^{th}$ pair of electrodes, and where i is the number of the exciting pair of electrodes, j is the number of the measuring pair of electrodes, $$f_1^i(j)$$

is the given distribution of voltage between adjacent electrodes along the boundary of the reference object, $$f_2^i(j)$$

are signals caused by spurious couplings, and $$c_\alpha^i \ (\alpha = 1, 2, 3)$$

are the approximating coefficients of the measured distribution of the potential differences; and;
   f. computer means to reconstruct the image of the spatial distribution of conductivity of said body by back projection along equipotential lines according to the expressions:

$$S = \sum \frac{W^{lt} W^{rt}}{W^{lt} + W^{rt}} (\lambda^{lt} + \lambda^{rt})$$

$$\lambda^{lt,rt} = u_r^{lt,rt} / u_m^{lt,rt} - 1$$

where $W^{lt}$, $W^{rt}$ are weighting factors determined according to the procedure of back projection in the direction from the left and from the right intersection of the equipotential line with the surface of said body, S is summed over all positions of the injecting electrodes, $$u_m^{lt,rt}$$

are voltages measured on the left and on the right ends of the equipotential line that passes through the given point of the reconstructed cross section, and $$u_r^{lt,rt}$$

are the reference potential differences corresponding to a body with homogeneous conductivity.

8. The device of claim 7, wherein said current source means is connected to a pair of diametrically opposite electrodes.

9. The device of claim 7, wherein said current source means is produced by a pulsed voltage in the form of two periods of meander, shifted by 180 degrees in phase with a controlled amplitude that is established by an 8-bit code.

10. The device of claim 7, further including a comparator means by which voltages measured at other electrodes that fall outside an allowable range are flagged for attention.

* * * * *

UNITED STATES PATENT AND TRADEMARK OFFICE
CERTIFICATE OF CORRECTION

PATENT NO.    : 6,236,886 B1
DATED         : May 22, 2001
INVENTOR(S)   : Cherepenin et al.

It is certified that error appears in the above-identified patent and that said Letters Patent is hereby corrected as shown below:

<u>Title page, Item [54] and Column 1, lines 1-3,</u>
Title should read as follows:
-- [54] Title: METHOD OF OBTAINING OF TOMOGRAPHIC IMAGE OF A BODY AND ELECTRIC IMPEDANCE TOMOGRAPH --

Signed and Sealed this

Tenth Day of December, 2002

JAMES E. ROGAN
*Director of the United States Patent and Trademark Office*